US011553888B2

(12) United States Patent
Hindorf et al.

(10) Patent No.: US 11,553,888 B2
(45) Date of Patent: Jan. 17, 2023

(54) APPARATUS FOR RADIOPHARMACEUTICAL QUANTIFICATION OF A BODY PART

(71) Applicant: Bayer Aktiengesellschaft, Leverkusen (DE)

(72) Inventors: Cecilia Hindorf, Lund (SE); Erik Larsson, Sjöbo (SE); Gustav Brolin, Lund (SE); Tomas Ohlsson, Lund (SE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 16/633,811

(22) PCT Filed: Jul. 23, 2018

(86) PCT No.: PCT/EP2018/069893
§ 371 (c)(1),
(2) Date: Jan. 24, 2020

(87) PCT Pub. No.: WO2019/020554
PCT Pub. Date: Jan. 31, 2019

(65) Prior Publication Data
US 2020/0170597 A1    Jun. 4, 2020

(30) Foreign Application Priority Data

Jul. 25, 2017   (EP) .................................. 17183069
Oct. 10, 2017   (EP) .................................. 17195657

(51) Int. Cl.
*A61B 6/00*      (2006.01)
*G06T 7/00*      (2017.01)

(52) U.S. Cl.
CPC ............ *A61B 6/481* (2013.01); *A61B 6/4258* (2013.01); *A61B 6/5205* (2013.01); *G06T 7/0012* (2013.01); *G06T 2207/10116* (2013.01)

(58) Field of Classification Search
None
See application file for complete search history.

(56) References Cited

U.S. PATENT DOCUMENTS

2002/0039401 A1*   4/2002   Salb ............... A61B 6/4241
                                              378/98.9
2014/0044642 A1*   2/2014   Hefti ............. A61K 51/0455
                                              424/1.73

FOREIGN PATENT DOCUMENTS

JP     9318755     * 12/1997
JP     H09318755 A   12/1997
RU     2428930 C1  *  9/2011

OTHER PUBLICATIONS

Hutton, B.F. et al. (2011). "Review and current status of SPECT scatter correction", Physics in Medicine and Biology, 56(14): R85-R112. (Year: 2011).*

(Continued)

*Primary Examiner* — Vu Le
*Assistant Examiner* — Courtney Joan Nelson
(74) *Attorney, Agent, or Firm* — Morrison & Foerster LLP

(57) ABSTRACT

An apparatus for radiopharmaceutical quantification of a body part includes a processor configured to receive at least one gamma image of a body part acquired by at least one gamma camera configured to detect gamma and/or X-rays. The at least one gamma image comprises spectral energy data that includes data resulting from decay of at least one radiopharmaceutical. The processor is configured to determine an activity of the at least one radiopharmaceutical at a plurality of spatial positions in the body part and determines a spatial distribution of the at least one radiopharmaceutical in the body part. The determination for a spatial position of the plurality of spatial positions comprises correlating a generated synthetic spectrum to an experimental spectrum (Continued)

generated from the spectral energy data for at least one position in the at least one gamma image that corresponds to that spatial position.

15 Claims, 12 Drawing Sheets

(56) References Cited

OTHER PUBLICATIONS

Macey, D.J. et al. (1995)." Improved conjugate view quantitation of 1-131 by subtraction of scatter and septal penetration events with a triple energy window method," Medical Physics 22(10): 1637-1643. (Year: 1995).*
Machine translation of RU-2428930-C1 (Year: 2011).*
Machine translation of JP9318755 (Year: 1997).*
Hutton, B.F. et al. (2011). "Review and current status of SPECT scatter correction", Physics in Medicine and Biology, 56(14): R85-R112.
Macey, D.J. et al. (1995)." Improved conjugate view quantitation of 1-131 by subtraction of scatter and septal penetration events with a triple energy window method," Medical Physics 22(10): 1637-1643.
Robertson, A.K.H. et al. (2017). "Multi-isotope SPECT imaging of the 225AC decay chain: feasibility studies," Phys. Med. Biol. 62(11): 4406-4420.

* cited by examiner

Anterior count image
[215,260] keV ($^{227}$Th)

Anterior count image
[135,165] keV ($^{223}$Ra)

Present method
$^{227}$Th activity image

Present method
$^{223}$Ra activity image

APPARATUS FOR RADIOPHARMACEUTICAL QUANTIFICATION OF A BODY PART

CROSS REFERENCE TO RELATED APPLICATIONS

This application is a national stage application under 35 U.S.C. § 371 of International Application No. PCT/EP2018/069893, filed internationally on Jul. 23, 2018, which claims the benefit of priority to European Application Nos. 17183069.8, filed Jul. 25, 2017, 17195657.6, filed Oct. 10, 2017.

FIELD OF THE INVENTION

The present invention relates to an apparatus for radiopharmaceutical quantification of a body part, to a system for radiopharmaceutical quantification of a body part, to a method for radiopharmaceutical quantification of a body part, as well as to a computer program element and a computer readable medium.

BACKGROUND OF THE INVENTION

The general background of this invention is quantitative gamma camera imaging of patients. Radiopharmaceuticals can be used in the treatment of patients. A radiopharmaceutical such as a radionuclide, or radionuclides, can be taken internally by a patient for example intravenously or orally. A radiopharmaceutical, such as a radionuclide can be useful in the detection of specific diseases, and indeed can also be used in the targeted treatment of diseases, where the emission of alpha particles/electrons/beta particles can be used to disrupt targeted tissue cells. (For ease of explanation, the following discussion relates in specific parts to radionuclides however, such discussion also applies more generally to radiopharmaceuticals). The location of the radionuclide within the patient is required to be determined for quantification and dosimetry. As the radionuclide decays, gamma rays can be emitted in certain decay processes and external cameras, such as gamma cameras or detectors, are used to capture these photons from which an image can be acquired. However, such gamma ray imaging poses particular problems even for a single radionuclide, due to for example a low photon emission yield of radionuclides and the inclusion in measurement data of a large background photon contribution from cosmic and terrestrial sources, for example when very low activities of the order of 1 MBq are administered to patients. Furthermore, gamma rays can undergo scattering, for example via Compton scattering, on the route from the decay site to the detector, and thus can appear to have originated elsewhere than the actual decay site. Gamma ray cameras, also termed gamma cameras, can make use of energy discrimination, so called energy windows, to exclude emitted photons that do not originate directly from a radioactive decay. However, there is still a requirement to further improve imaging capabilities, especially if there is more than one radionuclide present. This can occur, for example, if a particular radionuclide that is administered to a patient has a daughter radionuclide that itself decays and emits gamma rays.

SUMMARY OF THE INVENTION

It would be advantageous to have an improved apparatus for radiopharmaceutical, such as radionuclide, quantification in a body part. In the description below reference to a radionuclide can mean a radiopharmaceutical.

It should be noted that the following described aspects and examples according to some embodiments of the invention apply also for radiopharmaceutical quantification of a body part, the system for radiopharmaceutical quantification of a body part, the method for radiopharmaceutical quantification of a body part, and for the computer program element and the computer readable medium.

According to some embodiments, there is provided an apparatus for radiopharmaceutical quantification of a body part, comprising:

an input unit; and
a processing unit.

The input unit is configured to provide the processing unit with at least one photon image of a body part. The at least one photon image was acquired by at least one photon camera configured to detect gamma rays and/or X-rays. Here, a photon image can be a gamma image or gamma camera image, and the photon camera a gamma camera. The at least one photon (gamma) image comprises spectral energy data that comprises data that has resulted from the decay of at least one radiopharmaceutical. The input unit is also configured to provide the processing unit with characteristic photon emission energies and emission probabilities associated with the decay of the at least one radiopharmaceutical. The processing unit is configured to determine an activity of the at least one radiopharmaceutical at a plurality of spatial positions in the body part. The determination for a spatial position of the plurality of spatial positions comprises a correlation of a generated synthetic spectrum to an experimental spectrum generated from the spectral energy data for at least one position in the at least one photon (gamma) image that corresponds to that spatial position. The synthetic spectrum can be considered to be a model spectrum. The generation of the synthetic spectrum comprises utilisation of the photon emission energies and emission probabilities associated with the decay of the at least one radiopharmaceutical. The processing unit is also configured to determine a spatial distribution of the at least one radiopharmaceutical in the body part.

In other words, synthetic spectra that are generated from known data regarding radiopharmaceuticals (photon emission energies and emission probabilities) are matched or fitted to experimentally determined spectra, to enable the spatial distribution of one or more radiopharmaceuticals to be determined. Thus, when there is one radiopharmaceutical, by fitting synthetic spectra to acquired spectra, the effects of scattering and residual photons (e.g. gamma rays/X-rays) can be separated from the photons (e.g. gamma rays/X-rays/Bremsstrahlung) that originate directly from decay events. And, when there are for example two or more radiopharmaceuticals the overlapping contributions of the two or more radiopharmaceuticals can also be determined. Furthermore, this modelling also enables the primary photon (e.g. gamma ray and/or X-ray) contributions that originate from the actual decay of the radiopharmaceuticals to be differentiated from both scatter and attenuation events, where photons (e.g. gamma rays and/or X-rays) are either scattered or attenuated on the route to the photon (e.g. gamma ray and/or X-ray) camera (or detector) and also differentiated from background cosmic ray events. Thus, in addition to different radiopharmaceuticals being able to be differentiated in the body part, noise in the data can be reduced because the signals (scatter, background etc) that are not directly related to the decay event (primary signals) can also be differentiated from the primary signals.

The at least one photon (gamma) image can comprise at least one gamma ray image. The at least one photon (gamma) image can comprise at least one X-ray image. The at least one photon camera can be a gamma ray camera/gamma camera and/or X-ray camera. The at least one radiopharmaceutical can comprise at least one radionuclide. Thus for example, radiopharmaceuticals such as 227Th and/or I-123 and/or 223Ra can be utilized, which emit alpha particles/electrons/beta particles with the associated emission of photons such as gamma rays/X-rays (photons) and detection of these photons can be used to quantify the radiopharmaceutical in the body part.

In some embodiments, the input unit is configured to provide the processing unit with a half-life for the decay of the at least one radiopharmaceutical. The generation of the synthetic spectrum then comprises utilization of the half-life for the decay of the at least one radiopharmaceutical. In this way, the half-lives of, for example, 227Th and 223Ra can be used to calculate the "true" activities of 227Th and 223Ra.

In this manner, the decay characteristics of a first radiopharmaceutical can be taken into account in determining the spatial distributions of the first radiopharmaceutical in the body part. Also, when there are two or more radiopharmaceuticals the decay characteristics of the two or more radiopharmaceuticals can be taken into account in determining the spatial distributions of the first and second radiopharmaceutical in the body part.

In some embodiments, the at least one radiopharmaceutical comprises a first radiopharmaceutical and a second radiopharmaceutical.

In some embodiments, the second radiopharmaceutical is a product of the decay of the first radiopharmaceutical. Thus, a second radionuclide can be a product of the decay of a first radionuclide.

In other words, not only can mother and daughter radiopharmaceuticals be differentiated from one another, the information that the second radiopharmaceutical is derived from the first radiopharmaceutical can be used in generating the synthetic spectrum that is fitted to the real acquired spectrum.

However, the second radiopharmaceutical need not be derived from the first radiopharmaceutical, and could for example be Tc-99m or I-123.

In some embodiments, the input unit is configured to provide the processing unit with at least one time of acquisition of the at least one photon (gamma) image relative to a start time. The start time is defined as a time when the first radiopharmaceutical has not yet decayed to produce significant quantities of the second radiopharmaceutical. The generation of the synthetic spectrum then comprises utilization of the at least one time of acquisition of the at least one photon (gamma) image relative to the start time.

In other words, the expected relative quantities of the first to second radiopharmaceutical can be determined from knowledge of the time of image acquisition relative to the time when there was in effect 100% of the first radiopharmaceutical, or a known proportion of the first radiopharmaceutical to the second radiopharmaceutical. Thus, a reference time and half-lives can be used to calculate the expected activity of 227Th and 223Ra at the time-points when imaging was performed.

In some embodiments, the generation of the synthetic spectrum comprises a determination of attenuation of photons (e.g. gamma radiation) in the body part.

In some embodiments, the at least one photon (gamma) image comprises a first image and a second image, wherein the first image was acquired from a direction opposite a direction from which the second image was acquired.

In other words, the conjugate view technique can be used, from which only the total thickness of the body part at a particular position needs to be known in order for the attenuation of photons to be accurately modelled. Thus, the body can be taken to be formed from known materials and by knowing the total thickness of the body part the attenuation of photons can be accurately modelled.

In some embodiments, the input unit is configured to provide the processing unit with a plurality of total thicknesses of the body part for the plurality of spatial positions. Generation of the synthetic spectrum then comprises utilization of a total thickness of the body part at that spatial position.

In other words, the thickness of the body part can be used within the conjugate view technique, enabling the effect of attenuation to be accurately established. In some embodiments, the at least one photon (gamma) camera comprises a first photon (gamma) camera and a second photon (gamma) camera. Here reference to two cameras, can mean one camera having two detectors or can refer to two cameras each having a detector.

In this way, the first and second images can be acquired at the same time enabling temporally resolved data to be acquired. In some embodiments, the generation of the synthetic spectrum comprises determination of a spectral energy scatter component.

Thus, the effect of scatter photons, that have undergone for example Compton scattering on the route from the decay site to the detector (gamma camera), can be taken into account.

In some embodiments, the generation of the synthetic spectrum comprises determination of a spectral energy residual component.

Thus, photons (such as gamma rays/X-rays) that are background events, or from collimator penetration or partial energy deposition in the detector can be taken into account. In some embodiments, the generation of the synthetic spectrum comprises utilization of an energy resolution of the at least one photon (gamma) camera.

In other words, the energy resolution of the camera can be used in order to provide modelled spectra that match the acquired spectra. In an example, the generation of the synthetic spectrum comprises utilization of a photon detection efficiency of the at least one photon (gamma) camera.

According to some embodiments, there is provided system for radiopharmaceutical quantification of a body part, comprising:
  a photon acquisition unit;
  an apparatus for radiopharmaceutical quantification of a body part according to the first aspect; and
  an output unit.

The photon acquisition unit comprises at least one photon (gamma) camera. The photon acquisition unit is configured to provide the at least one photon (gamma) image. The output unit is configured to output an image that comprises the spatial distribution of the at least one radiopharmaceutical in the body part.

In some embodiments, there is provided a method for radiopharmaceutical quantification of a body part, comprising:
(a) providing a processing unit with at least one photon (gamma) image of a body part; wherein, the at least one photon (gamma) image was acquired by at least one photon (gamma) camera; and wherein, the at least one photon (gamma) image (gamma image) comprises spectral energy data that comprises data that has resulted from the decay of at least one radiopharmaceutical;

(b) providing the processing unit with characteristic photon emission energies and emission probabilities associated with the decay of the at least one radiopharmaceutical;

(c) determining by the processing unit an activity of the at least one radiopharmaceutical at a plurality of spatial positions in the body part, wherein, the determination for a spatial position of the plurality of spatial positions comprises step (c1) generating a synthetic spectrum and correlating the generated synthetic spectrum to an experimental spectrum generated from the spectral energy data for at least one position in the at least one photon (gamma) image that corresponds to that spatial position, and wherein, generating the synthetic spectrum comprises utilizing the photon emission energies and emission probabilities associated with the decay of the at least one radiopharmaceutical; and (d) determining by the processing unit a spatial distribution of the at least one radiopharmaceutical in the body part.

According to some embodiments, there is provided a computer readable medium having stored computer element as previously described.

Advantageously, the benefits provided by any of the above aspects equally apply to all of the other embodiments and vice versa.

BRIEF DESCRIPTION OF THE DRAWINGS

Exemplary embodiments will be described in the following with reference to the following drawings, and Table 1.

DETAILED DESCRIPTION OF EMBODIMENTS

Figure 1:
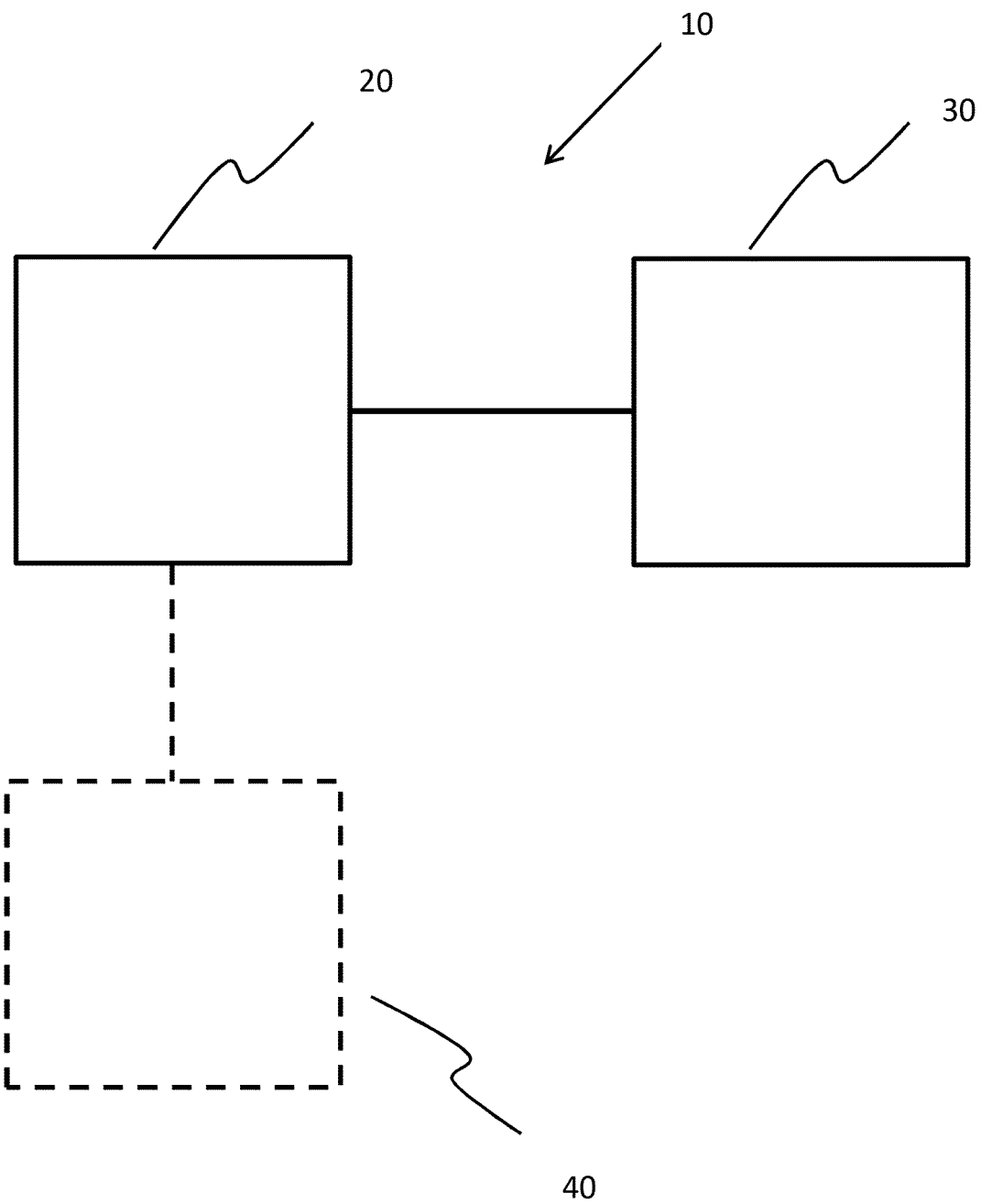
FIG. 1 shows a schematic set up of an example for radionuclide quantification of a body part.

FIG. 1 shows an example of an apparatus 10 for radiopharmaceutical quantification of a body part according to some embodiments. The specific example, and that relating to the other figures, relates to radionuclide quantification, where decay of at least one radionuclide has led to the emission of gamma rays and the generation of at least one gamma image of a body part. However, radiopharmaceuticals other than the radionuclide referred to below can be utilized (e.g. 223Ra, I-123), with for example images being X-ray images and the camera being an X-ray camera for example. Thus, the specific examples relating to the quantification of at least one radionuclide have wider applicability to the quantification of at least one radiopharmaceutical in the body part. Returning to the example of FIG. 1, the apparatus 10 comprises an input unit 20, and a processing unit 30. The input unit 20 is configured to provide the processing unit 30 with at least one gamma image of a body part. This is via wired or wireless communication. The at least one gamma image was acquired by at least one gamma camera. The at least one gamma image comprises spectral energy data that comprises data that has resulted from the decay of at least one radionuclide. The input unit 20 is also configured to provide the processing unit 30 with characteristic photon emission energies and emission probabilities associated with the decay of the at least one radionuclide. This is via wired or wireless communication. The processing unit 30 is configured to determine an activity of the at least one radionuclide at a plurality of spatial positions in the body part.

The determination for a spatial position of the plurality of spatial positions comprises a correlation of a generated synthetic spectrum to an experimental spectrum generated from the spectral energy data for at least one position in the at least one gamma image that corresponds to that spatial position. The generation of the synthetic spectrum comprises utilization of the photon emission energies and emission probabilities associated with the decay of the at least one radionuclide. The processing unit 30 is also configured to determine a spatial distribution of the at least one radionuclide in the body part. Thus count "images" from the at least one camera and the spatial distribution of those counts, can be used to map back to the spatial distribution of the at least one radiopharmaceutical (such as at least one radionuclide) in the body part.

In some embodiments, the photon emission energies and emission probabilities associated with the decay of the at least one radionuclide are provided from a database 40. Thus, the photon emission energies and emission probabilities associated with the decay of the first radionuclide and photon emission energies and emission probabilities associated with the decay of the second radionuclide are provided from the database 40. Where there are two radionuclides, at least one of those radionuclides can have daughter radionuclides.

In some embodiments, correlation of the generated synthetic spectrum to the experimental spectrum comprises generating a synthetic spectrum that most closely matches the experimental spectrum.

In some embodiments, the first radionuclide is Thorium 227. In some embodiments, the second radionuclide is Radium 223.

In some embodiments, the at least one position in the at least one gamma image that corresponds to the spatial position in the body part is associated with one pixel of the gamma camera and thus with one pixel in the image. Thus, the amount of the at least one radionuclide (that can be a first radionuclide and a second radionuclide) can be determined by fitting a theoretical spectrum to an experimental energy spectrum in each pixel. In this way, by considering each pixel of the camera, correlating with that in the image, the spatial distribution of the at least one radionuclide (e.g. first and second radionuclides) can be determined in the at least one image and hence within the body part. Here a "pixel" can be considered to be a "site of interaction" of the camera.

In some embodiments, the input unit is the at least one camera.

According to some embodiments, the input unit is configured to provide the processing unit with a half-life for the decay of the at least one radionuclide, and wherein the generation of the synthetic spectrum comprises utilization of the half-life for the decay of the at least one radionuclide.

According to some embodiments, the at least one radionuclide comprises a first radionuclide and a second radionuclide.

In some embodiments, a first radiopharmaceutical and a second radiopharmaceutical are administered to a patient, which in an example is a first radionuclide and a second radionuclide that are administered to the patient.

According to some embodiments, the second radionuclide is a product of the decay of the first radionuclide.

According to some embodiments, the input unit is configured to provide the processing unit with at least one time of acquisition of the at least one gamma image relative to a start time. The start time is defined as a time when the first radionuclide has not yet decayed to produce significant quantities of the second radionuclide. The generation of the synthetic spectrum then comprises utilization of the at least one time of acquisition of the at least one gamma image relative to the start time. Thus, this information can be used in determining the activity of the at least one radionuclide at the time of acquisition of the at least one image.

According to some embodiments, the generation of the synthetic spectrum comprises a determination of an attenuation of gamma rays along the projection.

In some embodiments, the determination comprises an exponential function of a product of distance and linear attenuation coefficient.

According to some embodiments, the at least one gamma image comprises a first image and a second image. The first image was acquired from a direction opposite a direction from which the second image was acquired. In some embodiments, anterior and posterior images can be acquired at the same time by two detectors of a camera or by two cameras having a detector each.

In some embodiments, the first image is acquired at a time that is different to the time of acquisition of the second image. In other words, a single gamma camera can be used to acquire the first and second image, through for example rotation of the camera relative to the body part.

According to some embodiments, the input unit is configured to provide the processing unit with a plurality of total thicknesses of the body part for the plurality of spatial positions. The generation of the synthetic spectrum then comprises utilization of a total thickness of the body part at that spatial position.

In some embodiments, the plurality of total thicknesses are provided on the basis of a scout scan that was acquired in addition to acquisition of the at least one gamma image. The scout scan can in an example be termed a CT localization image.

According to some embodiments, the at least one gamma camera comprises a first gamma camera and a second gamma camera.

According to some embodiments, the generation of the synthetic spectrum comprises determination of a spectral energy scatter component.

In some embodiments, the spectral energy scatter component is determined as a sum over the first and second nuclides and emission energies, modulated by emission yields and gamma camera efficiency.

According to some embodiments, the generation of the synthetic spectrum comprises determination of a spectral energy residual component.

In some embodiments, the spectral energy residual component is constant with respect to energy. This provides for simplification of modelling.

According to some embodiments, the generation of the synthetic spectrum comprises utilization of an energy resolution of the at least one gamma camera.

In some embodiments, utilization of the energy resolution of the at least one gamma camera comprises modelling the energy resolution using a Gaussian function.

According to some embodiments, the generation of the synthetic spectrum comprises utilization of a detector efficiency of the at least one gamma camera.

In some embodiments, utilization of the detector efficiency comprises utilization of a relative spectral efficiency. In an example, the relative efficiency of the detector is determined through Monte Carlo simulations. In an example, the relative spectral efficiency is determined through Monte Carlo simulations.

In an example, utilization of the gamma ray detection efficiency comprises calibration of the gamma camera.

Figure 2:
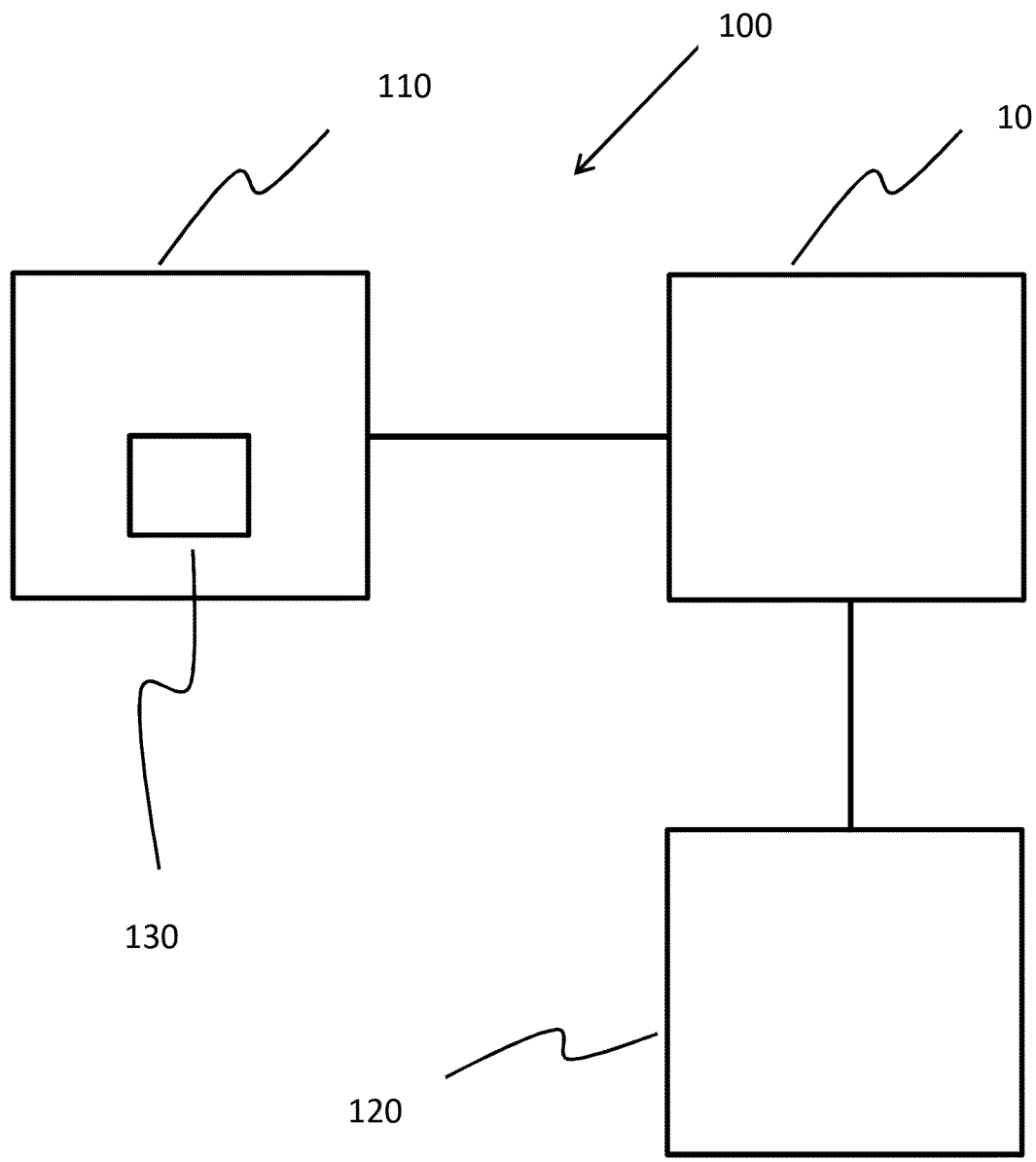
FIG. 2 shows a schematic set up of an example of a system for radionuclide quantification of a body part.

FIG. 2 shows an example of a system 100 for radionuclide quantification of a body part according to some embodiments, comprising:
- a gamma acquisition unit 110;
- an apparatus 10 for radionuclide quantification of a body part according to any of the examples described with respect to FIG. 1; and
- an output unit 120.

The gamma acquisition unit 110 comprises at least one gamma camera 130. The gamma acquisition unit 110 is configured to provide the at least one gamma image. The output unit 120 is configured to output an image that comprises the spatial distribution of the at least one radionuclide in the body part.

In some embodiments, the output unit is configured to output an image that comprises the spatial distribution of the first radionuclide in the body part and the spatial distribution of the second radionuclide in the body part.

Figure 3:
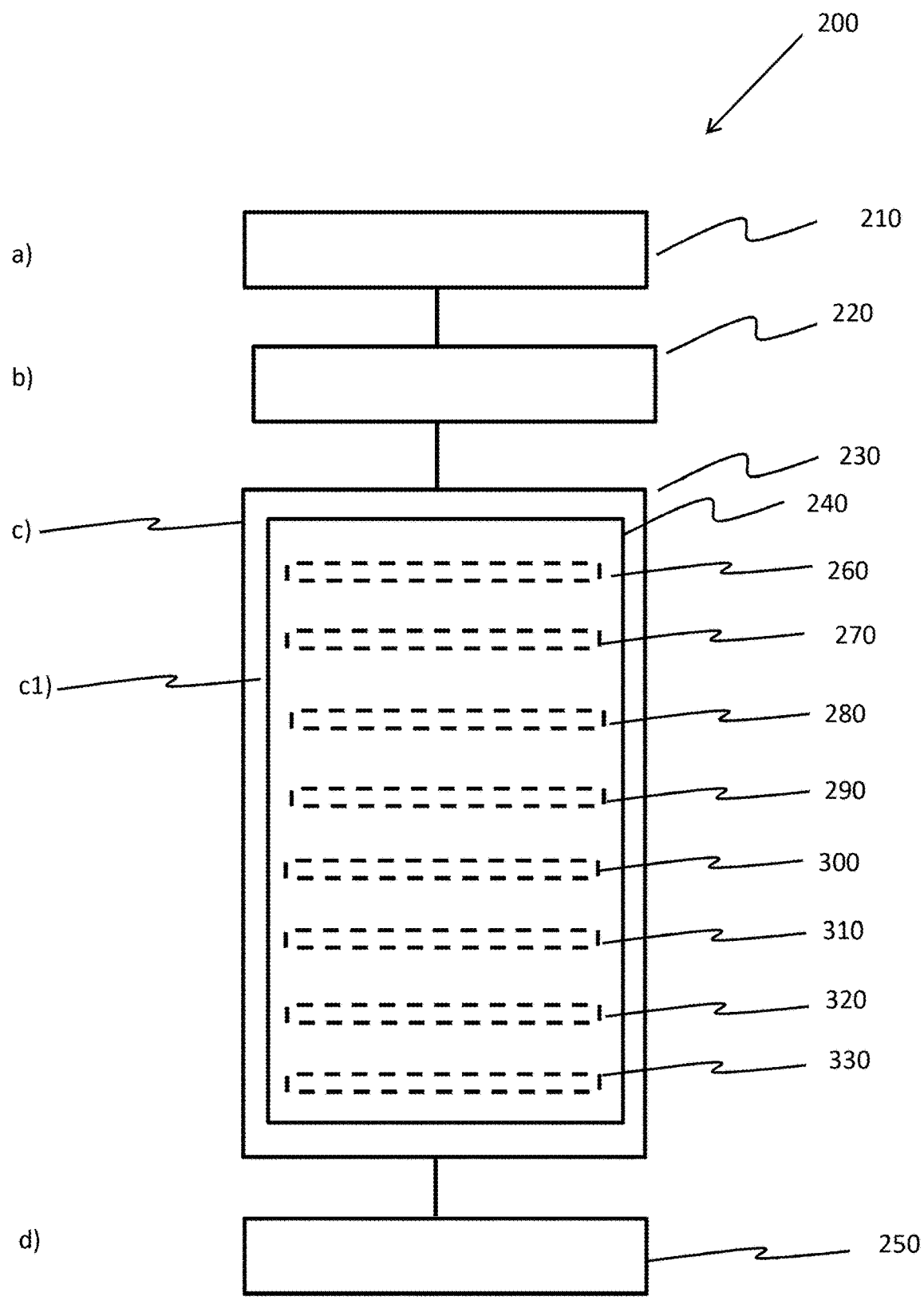
FIG. 3 shows a method for radionuclide quantification of a body part according to some embodiments.

FIG. 3 shows a method 200 for radionuclide quantification of a body part in its basic steps according to some embodiments. The method 200 comprises:

in a providing step 210, also referred to as step (a), providing a processing unit 30 with at least one gamma image of a body part; wherein, the at least one gamma image was acquired by at least one gamma camera; and wherein, the at least one gamma image comprises spectral energy data that comprises data that has resulted from the decay of at least one radionuclide;

in a providing step 220, also referred to as step (b), providing the processing unit with characteristic photon emission energies and emission probabilities associated with the decay of the at least one radionuclide;

in a determining step 230, also referred to as step (c), determining by the processing unit an activity of the at least one radionuclide at a plurality of spatial positions in the body part, wherein, the determination for a spatial position of the plurality of spatial positions comprises a generating step 240, also referred to as step (c1), that involves generating a synthetic spectrum and correlating the generated synthetic spectrum to an experimental spectrum generated from the spectral energy data for at least one position in the at least one gamma image that corresponds to that spatial position, and wherein, generating the synthetic spectrum comprises utilizing the photon emission energies and emission probabilities associated with the decay of the at least one radionuclide; and in a determining step 250, also referred to as step (d), determining by the processing unit a spatial distribution of the at least one radionuclide in the body part.

In some embodiments, an input unit 20 is configured to provide the processing unit 30 with the at least one gamma image.

In some embodiments, the input unit 20 is configured to provide the processing unit 30 with characteristic photon emission energies and emission probabilities associated with the decay of the first radionuclide and photon emission energies and emission probabilities associated with the decay of the second radionuclide.

In some embodiments, the at least one radionuclide comprises a first radionuclide and a second radionuclide.

In some embodiments, step (d) comprises utilizing 260 a half-life for the decay of a first radionuclide.

In some embodiments, step (d) comprises utilizing 270 a half-life for the decay of a second radionuclide.

In some embodiments, the input unit 20 is configured to provide the processing unit 30 with the half-life data.

In some embodiments, the second radionuclide is a product of the decay of the first radionuclide.

In some embodiments, step (d) comprises utilizing 280 at least one time of acquisition of the at least one gamma image relative to a start time, the start time defined as a time when the first radionuclide has not yet decayed to produce significant quantities of the second radionuclide.

In some embodiments, step (d) comprises determining 290 an attenuation of gamma rays in the body part.

In some embodiments, the at least one gamma image comprises a first image and a second image, wherein the first image was acquired from a direction opposite a direction from which the second image was acquired.

In some embodiments, the method comprises providing the processing unit with a plurality of total thicknesses of the body part for the plurality of spatial positions, and wherein step (d) comprises utilizing 300 a total thickness of the body part at that spatial position.

In some embodiments, the at least one gamma camera comprises a first gamma camera and a second gamma camera.

In some embodiments, the generation of the synthetic spectrum comprises determination of a spectral energy scatter component.

In some embodiments, step (c1) comprises determining 310 a spectral energy residual component.

In some embodiments, step (c1) comprises utilizing 320 an energy resolution of the at least one gamma camera.

In some embodiments, step (c1) comprises utilizing 330 a gamma ray detection efficiency of the at least one gamma camera.

The apparatus, system and method for radionuclide quantification of a body part are now described in more detail in conjunction with FIGS. 4-12 and Table 1.

The following relates to use of the above described apparatus, system and method for radionuclide quantification of a body part for the specific example of the simultaneous quantification of $^{227}$Th and $^{223}$Ra (including its daughter nuclides), aimed at patients undergoing targeted radionuclide therapy with $^{227}$Th. Gamma camera imaging in this setting poses a unique challenge due to the low activity administered (in the range of 1.4-7 MBq of $^{227}$Th), the low photon emission yield of the radionuclides, overlapping contributions from $^{227}$Th and $^{223}$Ra in the measurement data, in addition to a large background contribution from cosmic and terrestrial sources. It is to be noted that although the specific example relates to the quantification of $^{227}$Th and $^{223}$Ra, the methodology described here can be applied for the other radionuclides, where one radionuclide need not necessarily be derived from another radionuclide.

The Decay of $^{227}$Th and its Daughters $^{227}$Th decays in a seven-step serial decay into stable lead ($^{207}$Pb). The decay data for $^{227}$Th and its daughters are shown in Table 1. Alpha particles account for 96% of the 33.7 MeV which is released on average in the serial decay, whilst beta particles and conversion electrons account for 3%. Only 1% of the total energy is released as gamma radiation and characteristic X-rays. The low amount of activity that is used in alpha-particle radionuclide therapy, in combination with the low photon yield in the decay of these nuclei, is therefore a challenge for quantitative imaging, as described above and which has been addressed by the presently described, apparatus, system and method for radionuclide quantification of a body part.

Referring to Table 1, $^{227}$Th decays into $^{223}$Ra with a half-life ($T_{1/2}$) of 18.7 days. The daughter $^{223}$Ra in turn decays with a half-life of 11.4 days. This means that the amount of $^{223}$Ra present in a sealed sample of $^{227}$Th will increase with time ("build-up") and will after approximately 21 days onward exceed the $^{227}$Th activity.

The $^{227}$Th activity, $A_{Th}$, follows an exponential decay:

$$A_{Th}(t)=A_{Th}(0)e^{\lambda_{Th}t} \quad (1)$$

Where $\lambda$ is the decay constant given by $$\frac{\ln(2)}{T_{1/2}}.$$

The $^{223}$Ra activity, $A_{Ra}$, can be written as:

$$A_{Ra}(t) = A_{Th}(0) \cdot \frac{\lambda_{Ra}}{(\lambda_{Ra} - \lambda_{Th})}(e^{(-\lambda_{Th}t)} - e^{(-\lambda_{Ra}t)}) + A_{Ra}(0)e^{(-\lambda_{Ra}t)} \quad (2)$$

Where $A_{Th}(0)$ and $A_{Ra}(0)$ is the initial activity of $^{227}$Th and $^{223}$Ra at time t=0 respectively.

Figure 4:
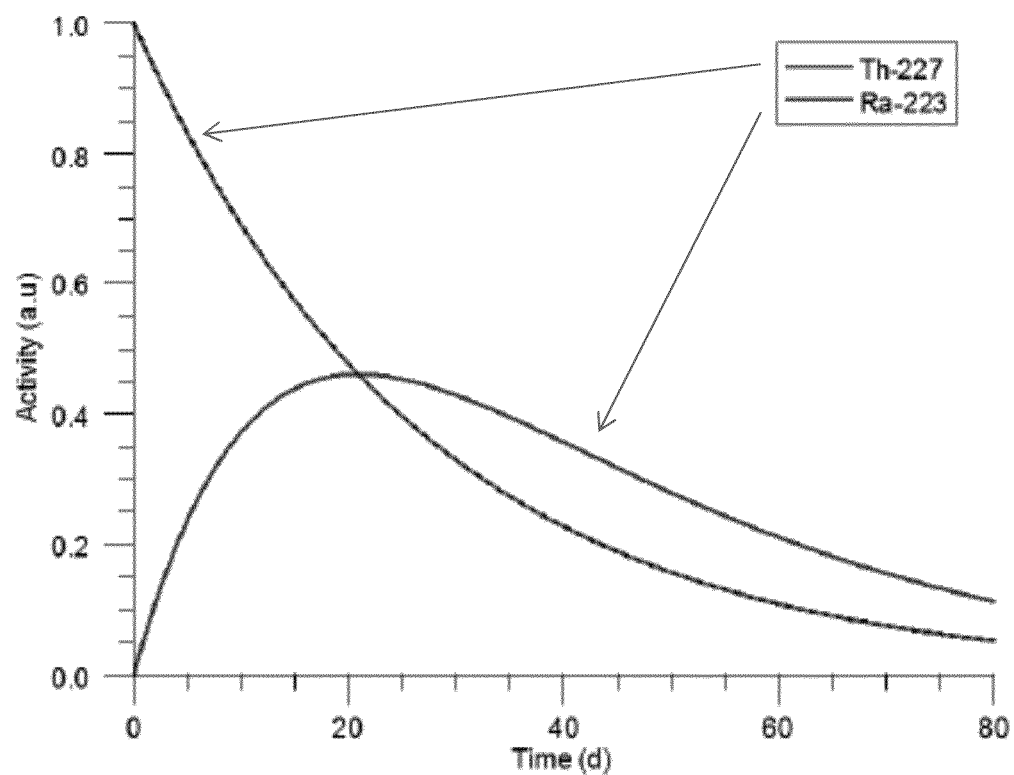
FIG. 4 shows an example of relative activities of $^{227}$Th and $^{223}$Ra.

FIG. 4 illustrates the decay of $^{227}$Th and build-up and decay of $^{223}$Ra as a function of time after chemical separation (i.e. assuming a sample of pure $^{227}$Th at t=0), calculated using equations (1) and (2). As shown in Table 1, the other daughters have very short half-lives relative to $^{223}$Ra, meaning that they can be considered to be intermediate, and practically instant, steps in the transition from $^{223}$Ra to $^{207}$Pb. However, following the discussion presented here the transition $^{211}$Pb→$^{211}$Bi with a half-life of 36 min could be taken into consideration if necessary. Thus, in this discussion $^{223}$Ra can be considered to be in equilibrium with its daughters.

Gamma Camera Energy Spectrum of $^{227}$Th and $^{223}$Ra with Daughters

Figure 5:
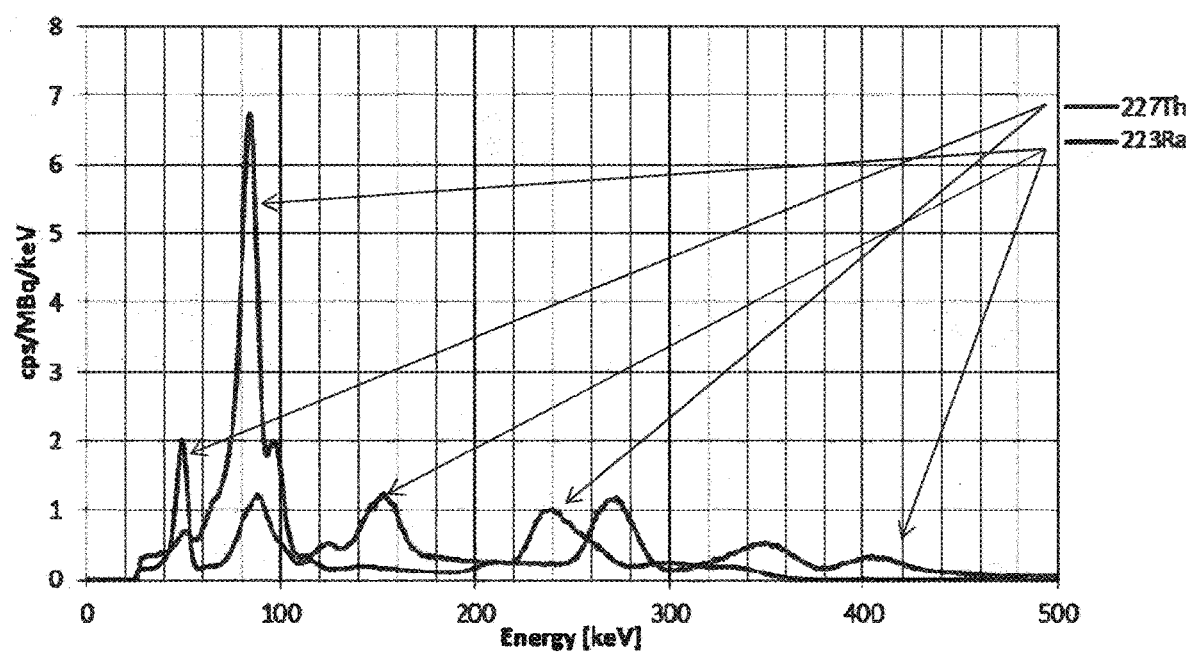
FIG. 5 shows an example of an acquired energy spectra of $^{227}$Th and $^{223}$Ra.

There are 34 different photon emissions with probability higher than 1% emitted in the decay chain of $^{227}$Th/$^{223}$Ra, in the energy range of approximately 10-830 keV. FIG. 5 shows acquired energy spectra for sources with pure $^{227}$Th and $^{223}$Ra in equilibrium with its daughters, respectively. The sources have been measured "in air", and as such there can be considered to be no scattering present between the source and the gamma camera. As discussed above, normally, gamma camera images are acquired by using hardware energy discrimination, i.e. energy acceptance windows centered around one or a few of the discrete photon energies. However, as shown in FIG. 5, regardless of where an energy acceptance window is positioned, there will be a signal contribution from both isotopes (nuclides) to the total signal, and thereby difficulties are presented in separating the signals from each other, if there is a spatial overlap between $^{227}$Th and $^{223}$Ra. Furthermore, even when there is only one radionuclide it can be difficult to differentiate between primary events (gamma rays that come directly from a decay site) from gamma rays that have been scattered or come from the cosmic background for example. Continuing the discussion relating to $^{227}$Th and $^{223}$Ra the energy region above 390 keV is however free from the $^{227}$Th signal, but due to low count rate and insufficient photon collimation (decay positioning) at these high energies, this energy region for this case is suboptimal for imaging. Therefore, the gamma camera has been optimized for the detection of photons with energies from about 50 to 350 keV, meaning that the number of emissions actually contributing to the useful signal is lower than that shown in FIG. 5. Rather than use an energy acceptance window, the presently described apparatus, system and method for radionuclide quantification of a body part relies on spectral image data, i.e. data sets composed of energy spectra either for the entire image or for individual pixels in the image.

Energy Spectrum Model and Fitting to Measurement Data

According to some embodiments, the presently described apparatus, system and method for radionuclide quantification of a body part improves the image quality, improves radionuclide separation and improves quantitative performance. The new method is based on fitting a theoretical model to the acquired energy spectrum in each gamma image. The theoretical model describes how the detected energy spectrum should look. The theoretical model makes use of physical principles relating to radiation propagation, and known decay data for the radionuclides, which can be found in databases. Additionally, use is made of relevant properties of the detector, which have been characterized.

The following describes the development of the method:

Photons emitted from a radioactive source can either travel directly to, and be absorbed by, the gamma camera detector, or they can interact in the patient, change direction and lose energy before they are detected. Other possible alternatives are that a high energy photon passes through the camera without interaction, or scatters somewhere else in the surroundings and is subsequently absorbed in the detector crystal. Although no two detected photons have the same origin and way to the detector, it is possible to model the spectrum as now described. The energy spectrum has been modelled as a sum of three components: 1) a primary component P, 2) a scatter component S and 3) a residual component R according to:

$$\hat{N}(E)=P(E)+S(E)+R(E) \quad (3)$$

The primary component of the energy spectrum represents the photons that have traveled directly from the decay position to the detector and are fully absorbed in the crystal. The scatter component represents the photons that have changed direction and lost energy on their way to the detector. The third component, the residual, represents other possible events that contribute to the measured spectra, e.g. photons that have scattered in the collimator or other parts of the camera before being detected. These individual components, and how they have been modelled, are discussed in more detail below.

Figure 6:
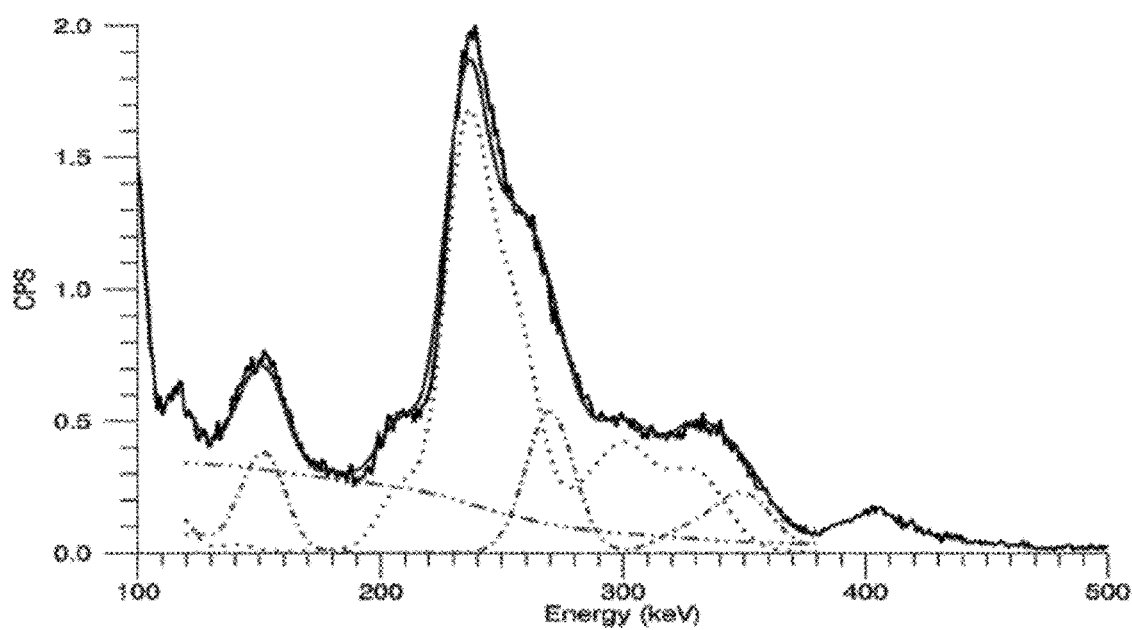
FIG. 6 shows an example of an acquired energy spectrum from a source containing $^{227}$Th and $^{223}$Ra, and a fitted modelled energy spectrum.

To illustrate operation of the model, FIG. 6 shows such an acquired energy spectrum (solid line—with noise) for gamma emission from both $^{227}$Th and $^{223}$Ra nuclides within a patient. A synthetic energy spectrum (solid line—smooth) has been fitted to the acquired data. In FIG. 6, the synthetic energy spectrum that has been fitted to the real acquired data has accounted for primary photons from both $^{227}$Th and $^{223}$Ra nuclide decay events, which as described above relates to photons that have travelled from the decay site and been absorbed in the detector. The synthetic energy spectrum also takes into account the detector efficiency, detector energy resolution and photon attenuation and scattering in the patient as well as the residual gamma ray contribution. In FIG. 6 the primary $^{227}$Th component (dotted line) and primary $^{223}$Ra (dashed-single dotted line), which has been calculated on a pixel by pixel basis enables the spatial distributions of these radionuclides to be presented on acquired image data; the fitting parameters of the primary component equals the activity of $^{227}$Th and $^{223}$Ra, respectively.

In FIG. 6 the scatter component (dash-triple dotted line) and attenuation of gamma rays through the patient have been taken account of, as has the residual of background signal (which is not shown in FIG. 6). Thus, because contributions to the signal other than the primary contributions have been determined and the effects of signal attenuation have also been taken into account, the accuracy of the primary contributions is improved and the noise is reduced.

Thus, by performing the model fitting on a pixel-by-pixel basis, it is possible to obtain two-dimensional images of the spatial distribution of the two radionuclides, and in the case of one radionuclide to improve the image quality. Therefore, in summary the methodology provides an improved image quality, radionuclide separation, and resilience to counting statistic noise, compared to what is obtained with conventional methods relying on energy windows acquisition.

Primary Component

In an ideal scenario, the gamma camera would detect all emitted photons from the radioactive decay and measure their energy with perfect accuracy. The peaks in the energy spectrum would be very narrow, with a height proportional to the activity of the radionuclide and the probability of emission. However, the detector is not ideal. Photons will only be detected with a certain probability that depends on their energy, and the energy spectrum will show broad peaks centered around the photon energy due to the limited energy resolution of the detector. Furthermore, photons emitted from an internal source will be attenuated in the tissue of the patients by scattering and absorption, and thereby be lost from the full-absorption peak.

Figure 7:
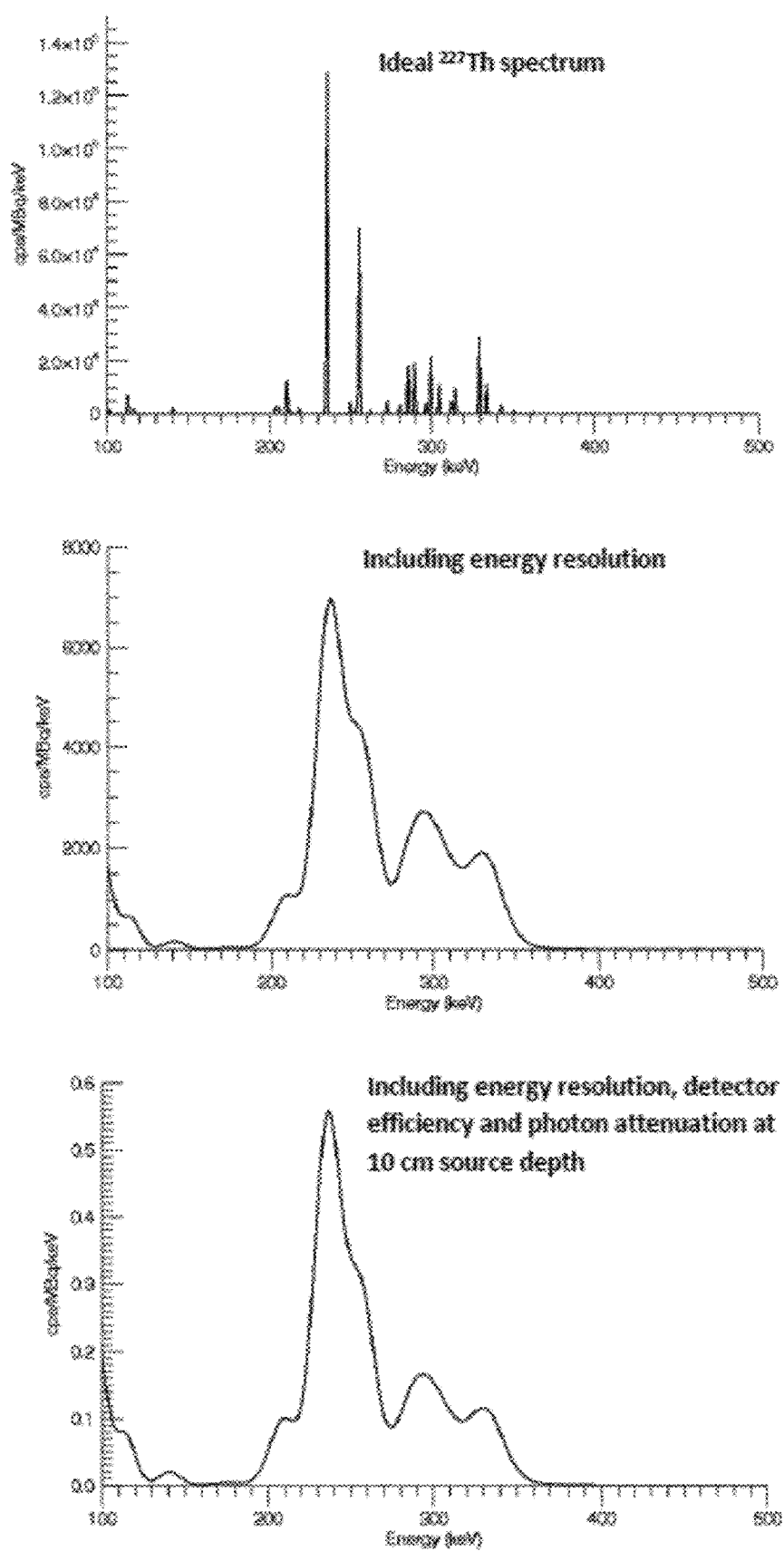
FIG. 7 shows an ideal $^{227}$Th energy spectrum, and a modelled energy spectrum including the effects of the resolution of a gamma camera used to acquire the spectral data, and a modelled energy spectrum including the effects of the resolution of a gamma camera and the effects of attenuation and detector efficiency.

FIG. 7 represents the above described situation. In FIG. 7 the primary component in the energy spectrum, exemplified for $^{227}$Th, has been modelled. In the top panel of FIG. 7 is shown an ideal spectrum, where all photons emitted from the $^{227}$Th decay are detected with perfect energy measurement. In the middle panel of FIG. 7 is shown an energy spectrum that includes the effect of imperfect energy measurements, i.e. limited energy resolution of the gamma camera. In the bottom panel of FIG. 7 is shown an energy spectrum that includes the effects of energy resolution, photon attenuation at a depth of 10 cm, and detector efficiency. Thus, FIG. 7 illustrates the ideal spectrum and the impact of the energy resolution of the gamma camera, the detector efficiency, and photon attenuation. It is seen that the energy resolution affects the visual characteristics of the spectrum, and that the detector efficiency and photon attenuation mainly affects the absolute detected values in terms of cps/MBq/keV.

The primary component $P_q$ for radionuclide q (i.e. $^{227}$Th or $^{223}$Ra) has been modelled as:

$$P_q(E) = (\Sigma_i \varepsilon(E_{q,i}) n_{\gamma,q,i} e^{-\mu(E_{q,i})d} G(E,E_{q,i}))) \quad (4)$$

where $\varepsilon(E_{q,i})$ is the detector efficiency for photon energy $E_{q,i}$, and $n_{\gamma,q,i}$ is the emission yield of photon i from the decay of nuclide q, and $e^{-\mu(E_{q,i})d}$ is the attenuation factor for photon i with energy $E_i$ originating from depth d, and $G(E,E_{q,i})$ is the energy resolution function given by equation (9), described below.

Figure 8:
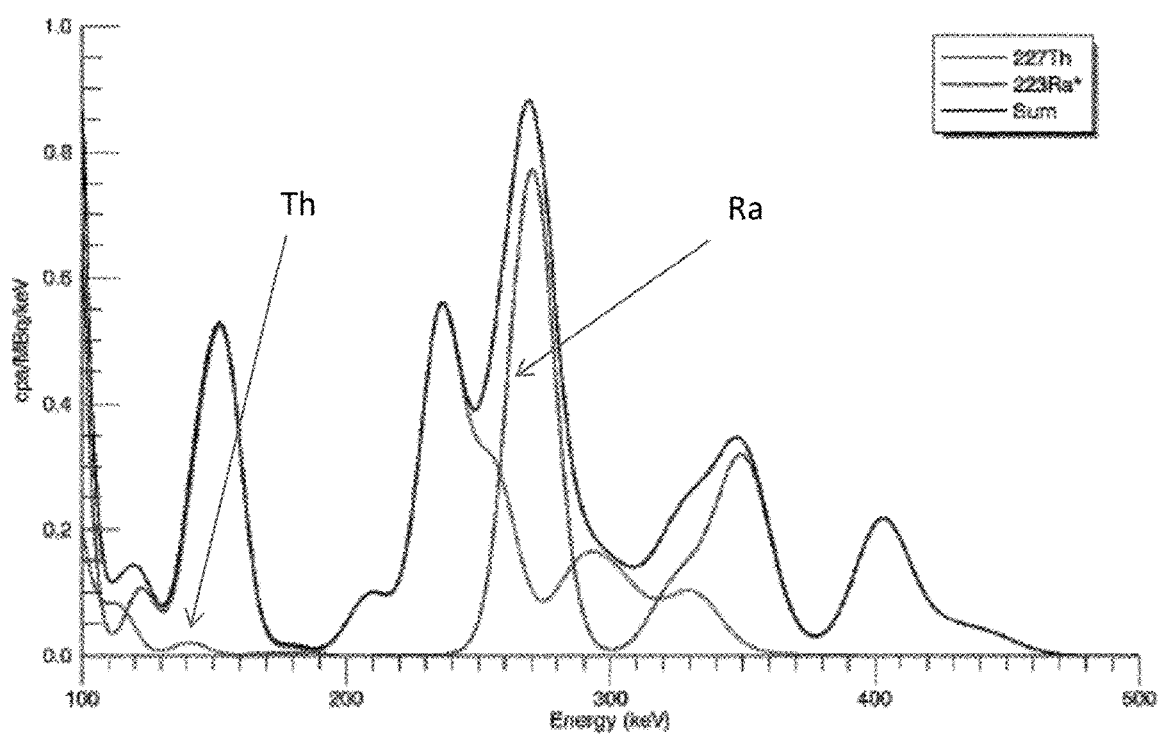
FIG. 8 shows a modelled energy spectrum for $^{227}$Th and $^{223}$Ra, showing the individual contributions of $^{227}$Th and $^{223}$Ra.

The primary component for the mixed $^{227}$Th/$^{223}$Ra spectrum has therefore been modelled as:

$$P(E) = \Sigma_q A_q P_q(E) \quad (5)$$

where $A_q$ is the activity [MBq] of nuclide q which is derived by fitting the model, as described above, to a measured spectrum. FIG. 8 shows an example of the primary component $P_q$ for $^{227}$Th and $^{223}$Ra as well as the sum of their contributions. For the data shown, $A_{Th} = A_{Ra} = 1$ MBq. In FIG. 8, the primary component $P_q$ of the energy spectrum model for $^{227}$Th and $^{223}$Ra has been calculated using equation (4), with the summed contributions calculated using equation (5), with equal activities $A_{Th} = A_{Ra} = 1$ MBq. The asterisk (*) indicates that $^{223}$Ra has been assumed to be in equilibrium with its daughters.

Scatter Component

Figure 9:
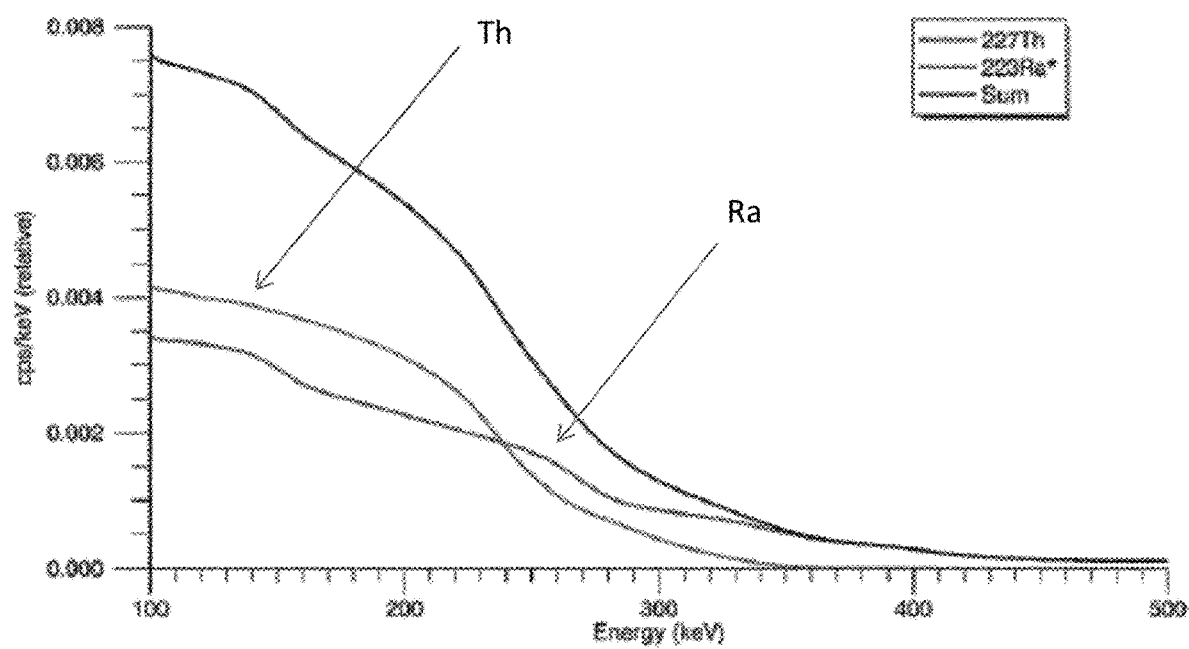
FIG. 9 shows a modelled scatter component of an energy spectrum for $^{227}$Th and $^{223}$Ra, showing the individual contributions of $^{227}$Th and $^{223}$Ra.

In addition to the primary photons, i.e. the photons that travel directly from the decay site to the detector, there is also a contribution from photons that have undergone Compton scattering in the patient prior to detection. The scattered photons produce an undesired signal contribution, in the sense that they do not originate from the position of radioactive decay and thereby produce counts in the gamma image at positions where there is no radioactivity. The energy of a scattered photon is always lower than the original photon that was scattered and could in theory be discriminated from primary photons by measurement of its energy. However, as discussed in the previous section, the energy resolution of the detector is not generally commensurate with that required for adequate discrimination. Instead, in the present apparatus, system and method for radionuclide quantification of a body part the contribution from scattered photons in the measured spectra has been modelled. This has been done by calculating that the shape of the scatter contribution $S_{q,i}(E)$ produced by a single photon energy $E_{q,i}$ can be approximated by the expression:

$$s_{q,i}(E) = \frac{1}{\left(1 + \left(\frac{E}{E_{q,i}}\right)^\gamma\right)} \quad (6)$$

where γ is a parameter describing the slope ("sharpness") of the transition from 1 to 0. In a manner similar to that for the primary component, the full scatter component is modelled as a sum over the radionuclides and emission energies, modulated by the emission yields and the detector efficiency according to:

$$S(E) = \Sigma_q B_q S_q = \Sigma_q B_q (\varepsilon(E) \Sigma_i n_{\gamma,q,i} s_{q,i}(E)) \quad (7)$$

where the fitting parameters $B_q$ are scatter amplitudes. The scatter amplitude is a measure of the amount of scattered photons in the measured spectrum. FIG. 9 illustrates the scatter components $S_q$ for $^{227}$Th and $^{223}$Ra individually of the energy spectrum model, calculated using equation (7) as well as the sum of their contributions. In this example, it has been taken that $B_{Th} = B_{Ra}$. The asterisk (*) indicates that $^{223}$Ra has been assumed to be in equilibrium with its daughters.

Residual Component

The residual component should in principle represent all other detected photons that cannot be considered to be either primary photons or those photons that have been scattered in the patient. The residual photons can instead originate, for example, from collimator penetration and partial energy deposition in the detector crystal, from scattering in the detector head, the collimator, couch or from somewhere else in the scanner room. In addition, there can be an elevated contribution from background cosmic and terrestrial radiation that is not fully compensated by the background subtraction, with background subtraction discussed below. These contributions are merged into a residual component, which has been modelled as being a constant with respect to energy, i.e.

$$R(E) = C \quad (8)$$

This approach is clearly a simplification of the actual residual contribution, however it has been found to be sufficient to obtain required fitting of modelled synthetic energy spectra to acquired energy spectra, and such a simplification also provides for computational efficiency.

Model Inputs

To model the measured spectra and thereby assure that the fitting parameters $A_q$ accurately reflect pixel activity, fixed model parameters need to be established. The photon emission energies ($E_q$,) and probabilities ($n_\gamma$,,), and half-lifes ($T_{1/2}$) have been established by the nuclear physics community over previous decades for radionuclides. For example, relevant fixed model parameter data can be collected from the NuDat 2 interface of the National Nuclear Data Center, nndc.bnl.gov/nudat2/. Other fixed parameters include those relating to photon attenuation and the characteristic of the specific gamma camera used, such as its spectral energy resolution and detector efficiency.

Gamma Camera Energy Resolution

As shown in FIGS. 6 and 7, the finite energy resolution of the gamma camera leads to broadening of the features in the energy spectrum. The energy resolution of the gamma camera has been modelled analytically using Gaussian functions ($E$,,) with unit area centered at energy $E_{q,i}$ according to:

$$G(E, E_{q,i}) = \frac{1}{\sqrt{2\pi}\sigma(E_{q,i})} e^{\frac{-(E-E_{q,i})^2}{2(\sigma(E_{q,i}))^2}} \quad (9)$$

where the standard deviation (width) a is energy-dependent and has been modelled as:

$$\sigma(E) = \sigma(E_{ref})\sqrt{\frac{E}{E_{ref}}} \qquad (10)$$

where $\sigma(E_{ref})$ is a known energy resolution at a reference energy $E_{ref}$. In this particular example, $E_{ref}$ was set at 236 keV, corresponding to the photon energy of the most prominent photon emission from $^{227}$Th. The energy resolution ($E_{ref}$), at this reference energy, was set to 8%—thus 8%@236 keV. This value was arrived at by manual tuning to match the width of the 236 keV peak in the model spectrum to the corresponding width in a measured spectrum. For specific gamma cameras a similar manual tuning process can be undertaken in order to model its energy resolution, or it can be measured explicitly.

Detector Efficiency

Figure 10:
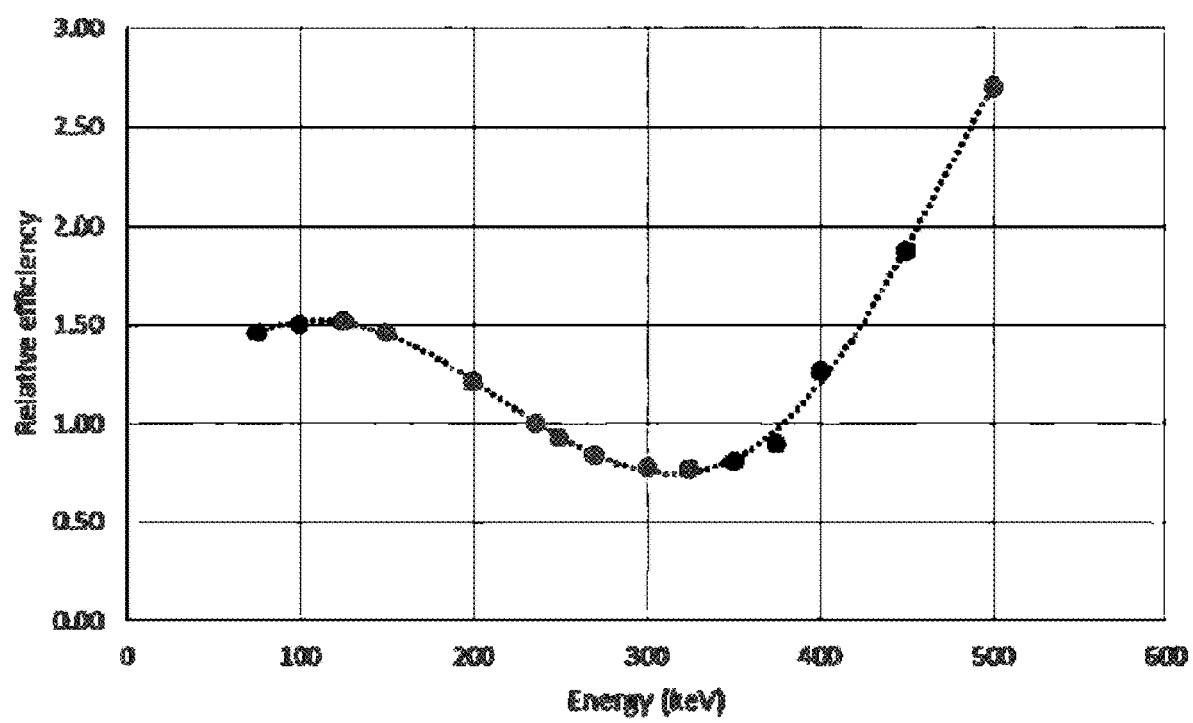
FIG. 10 shows a normalized detector efficiency as a function of energy.

The detector efficiency has been defined as the ratio of the number of photons detected in the full absorption-peak to the number of photons emitted by the source. The efficiency of the detector depends on the incoming photon energy in a non-trivial manner. To determine this, a Monte Carlo simulation was used to simulate mono-energetic photons with various energies impinging on the gamma camera. From these simulations the relative efficiency as a function of energy was derived, which is illustrated in FIG. 10. The relative efficiency curve has been normalized to unity at 236 keV. Further details on the use of such Monte Carlo simulations can be found in the following paper: Michael Ljungberg, Sven-Erik Strand, A Monte Carlo program for the simulation of scintillation camera characteristics, Computer Methods and Programs in Biomedicine, Volume 29, Issue 4, 1989, Pages 257-272, ISSN 0169-2607.

To convert the relative efficiency to an absolute efficiency, gamma camera measurements of a sample with a known activity of $^{227}$Th and $^{223}$Ra (produced by decay of $^{227}$Th) was carried out, without any attenuating and scattering material between the detectors and the source. The measurements were performed on four different occasions so that the activities of $^{227}$Th and $^{223}$Ra were varied. The activities were quantified, as described above (assuming no attenuation), and the absolute efficiency was determined through tuning to the known activities for both radionuclides at all four time points.

Photon Attenuation

As discussed above, the spectral model is separated into a primary component and a scatter component, and the impact of attenuation has been modelled on the primary component only. The attenuation of primary photons of energy E emitted from a source at depth d is given by $e^{-\mu(E)}$, where $\mu$ is the linear attenuation coefficient of the medium in which the source is located, at photon energy E. Linear attenuation coefficients can be found for example in a database compiled by NIST (National Institute of Standards and Technology) nist.gov/pml/xcom-photon-cross-sections-database.

One of the major drawbacks of planar gamma camera imaging is that the source depth in the projection direction (d) is unknown and therefore the attenuation can be difficult to estimate. However, energy spectra were acquired using the conjugate-view technique with two opposing projections to mitigate this issue. The conjugate-view technique is now briefly discussed:

Consider a hypothetical point source at depth $d_{ant}$ and $d_{post}$ from the anterior and posterior skin-surface, respectively, and that the patient/phantom thickness at the position of the source is $2d = d_{ant} + d_{post}$. The number of counts in the anterior and posterior projections are $N_{ant} = Ne^{-\mu d_{ant}}$ and $N_{post} = Ne^{-\mu d_{post}}$, respectively, and the geometric mean $N_{GM}$ becomes:

$$N_{GM} = \sqrt{N_{ant} N_{post}} = \sqrt{N^2 e^{-\mu(d_{ant}+d_{post})}} = Ne^{-\mu d} \qquad (11)$$

Thus, the number of counts in the geometric mean is dependent only on the total thickness at the position of the source, and not on the source position in the depth direction. The conjugate-view methodology was implemented by modeling the primary photons using equation (5) with d taken as the half-thickness of the phantom/patient at a specific position, and the modelled spectrum was fitted to the spectrum acquired using the conjugate view technique.

The half-thickness at each position was determined on the basis of a Computer Tomography (CT) localizer image ("scout"). A series of phantom measurements were performed to obtain a calibration curve for the thickness as a function of the pixel value in the scout image.

Background Correction

Background correction of the acquired image data was performed by subtraction of the background image acquired over 10 h (10 hours), as follows:

$$I_c = I_{acq} - \frac{t_{acq}}{t_{bkg}} I_{bkg} \qquad (12)$$

where $I_c$ is the background-corrected image, $I_{acq}$ is the acquired image with acquisition duration $t_{acq}$, and $I_{bkg}$ is the background image with acquisition duration $t_{bkg}$ (=10 h). The background subtraction was performed for each pixel and energy bin separately.

Spatial Filtering

To mitigate the effects of the poor signal-to-noise ratio in the images, a spatial filter was applied prior to further processing and model fitting. All images, including the background, were convoluted with a normalized 5×5 smoothing kernel $k_s$. The spatial filtering was performed for each energy bin separately.

Pixel-by-Pixel Model Fitting

The fitting of the theoretical model to each pixel in the image was performed using software that utilized the MPFIT code library for IDL: The MPFIT Library for IDL, Craig B. Markwardt, is available at physics.wisc.edu/~craigm/idl/fitting.html. In summary, a modelled synthetic energy spectra is fitted to an acquired energy spectrum by minimizing the $\chi^2$-value (weighted sum of squared deviations between model and data) using the Levenberg-Marquardt technique. The minimizer requires an initial estimate for each of the fitting parameters. The initial estimates of $A_{Th}$ and $A_{Ra}$ in each pixel were estimated based on the counting rates in predefined energy windows and the detector efficiency at this energy. The minimizer also required that a measurement uncertainty is associated to each data point, in order to assign a weight when calculating the $\chi^2$-value. These uncertainties were calculated for each pixel and energy bin, assuming Poisson statistics of the raw data and propagating these uncertainties through the background correction and spatial filtering.

Results

Figure 11:
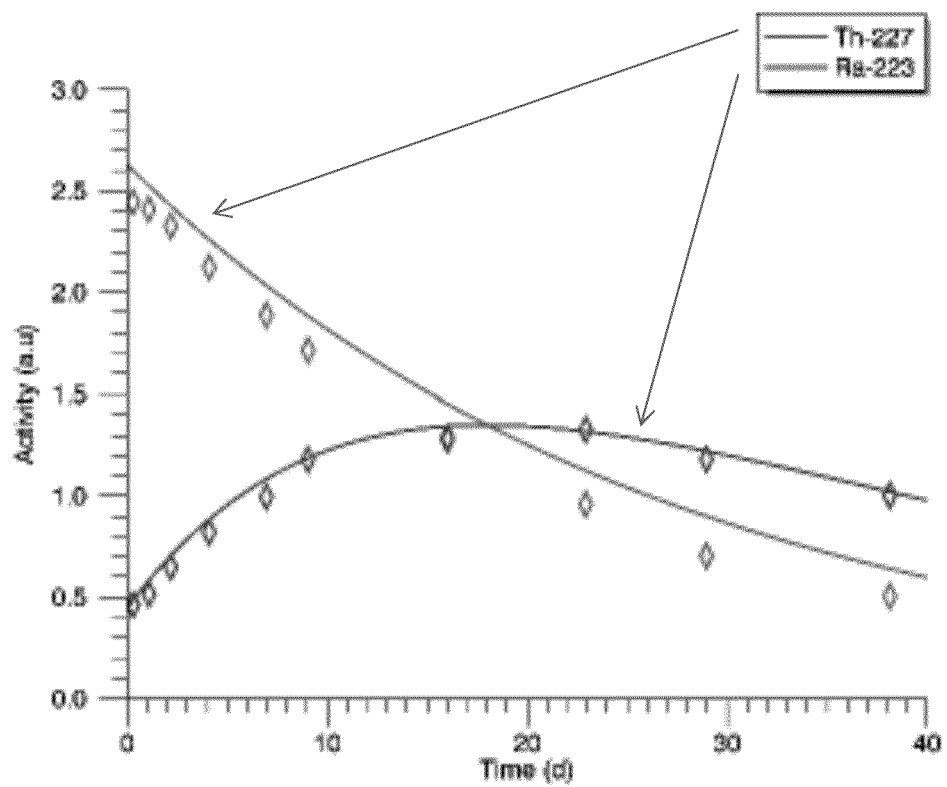
FIG. 11 shows an example of measured activities of $^{227}$Th and $^{223}$Ra and modelled activities for $^{227}$Th and $^{223}$Ra.
Figure 12:
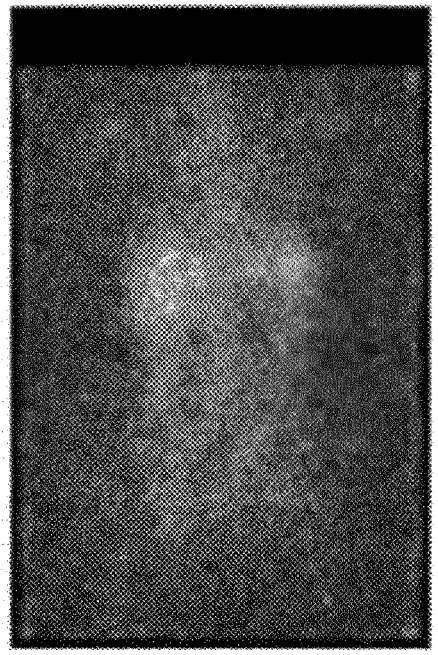
FIG. 12 shows raw activity images of a body part for $^{227}$Th and $^{223}$Ra at the top, and at the bottom are shown the activity images of the body part for $^{227}$Th and $^{223}$Ra that have been proceeded according to according to some embodiments of the described method for radionuclide quantification of a body part; and Table 1 shows decay data for $^{227}$Th and its daughters.
Figure 12:
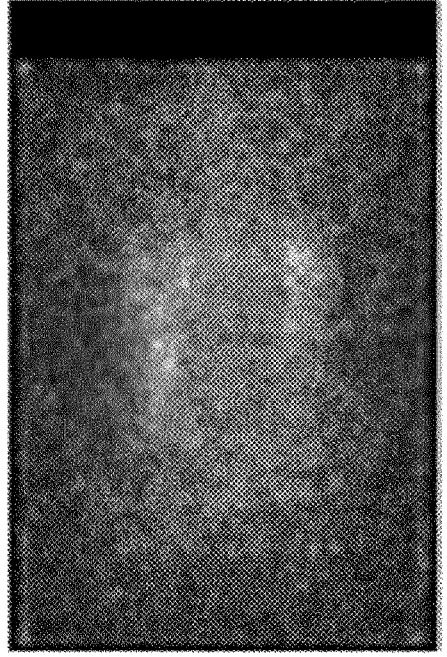
Figure 12:
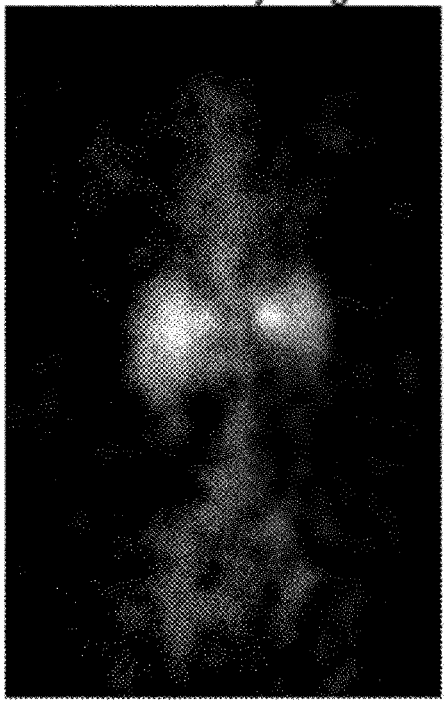
Figure 12:

FIG. 11 shows the total measured $^{227}$Th and $^{223}$Ra activity and the associated theoretical values determined through modelling given by equation (1) and (2). The measurement data captures the rate of decay and build-up well for both radionuclides (isotopes). The agreement between the measured and modelled activity indicates that the presently described apparatus, system and method provides for radionuclide quantification of a body part on the basis of gamma camera imaging of a body part containing radionuclides. This is exemplified in FIG. 12, which shows in the top two windows Anterior count images using energy windows (standard images/typical gamma camera images for imaging of $^{227}$Th and $^{223}$Ra, respectively, and in the bottom two windows shows activity images from the same patient using the presently described method for radionuclide quantification of a body part.

The following examples relate to the invention according to some embodiments:

Example 1. An apparatus for radiopharmaceutical quantification of a body part, comprising:
an input unit; and
a processing unit;
wherein, the input unit is configured to provide the processing unit with at least one photon image of a body part;
wherein, the at least one photon image was acquired by at least one photon camera configured to detect gamma rays and/or X-rays;
wherein, the at least one photon image comprises spectral energy data that comprises data that has resulted from the decay of at least one radiopharmaceutical;
wherein, the input unit is configured to provide the processing unit with characteristic photon emission energies and emission probabilities associated with the decay of the at least one radiopharmaceutical;
wherein, the processing unit is configured to determine an activity of the at least one radiopharmaceutical at a plurality of spatial positions in the body part,
wherein, the determination for a spatial position of the plurality of spatial positions comprises a correlation of a generated synthetic spectrum to an experimental spectrum generated from the spectral energy data for at least one position in the at least one photon image that corresponds to that spatial position, and
wherein, generation of the synthetic spectrum comprises utilization of the photon emission energies and emission probabilities associated with the decay of the at least one radiopharmaceutical; and
wherein, the processing unit is configured to determine a spatial distribution of the at least one radiopharmaceutical in the body part.

Example 2. Apparatus according to Example 1, wherein the input unit is configured to provide the processing unit with a half-life for the decay of the at least one radiopharmaceutical, and wherein the generation of the synthetic spectrum comprises utilization of the half-life for the decay of the at least one radiopharmaceutical.

Example 3. Apparatus according to any of Examples 1-2, wherein the at least one radiopharmaceutical comprises a first radiopharmaceutical and a second radiopharmaceutical.

Example 4. Apparatus according to Example 3, wherein the second radiopharmaceutical is a product of the decay of the first radiopharmaceutical.

Example 5. Apparatus according to any of Examples 3-4, wherein the input unit is configured to provide the processing unit with at least one time of acquisition of the at least one photon image relative to a start time, the start time defined as a time when the first radiopharmaceutical has not yet decayed to produce significant quantities of the second radiopharmaceutical, and wherein the generation of the synthetic spectrum comprises utilization of the at least one time of acquisition of the at least one photon image relative to the start time.

Example 6. Apparatus according to any of Examples 1-5, wherein the generation of the synthetic spectrum comprises a determination of an attenuation of photons in the body part.

Example 7. Apparatus according to any of Examples 1-6, wherein the at least one photon image comprises a first image and a second image, wherein the first image was acquired from a direction opposite a direction from which the second image was acquired.

Example 8. Apparatus according to Example 7, wherein the input unit is configured to provide the processing unit with a plurality of total thicknesses of the body part for the plurality of spatial positions; and wherein generation of the synthetic spectrum comprises utilization of a total thickness of the body part at that spatial position.

Example 9. Apparatus according to any of Examples 7-8, wherein the at least one photon camera comprises a first photon camera and a second photon camera.

Example 10. Apparatus according to any of Examples 1-9, wherein the generation of the synthetic spectrum comprises determination of a spectral energy scatter component.

Example 11. Apparatus according to any of Examples 1-10, wherein the generation of the synthetic spectrum comprises determination of a spectral energy residual component.

Example 12. Apparatus according to any of Examples 1-11, wherein the generation of the synthetic spectrum comprises utilization of an energy resolution of the at least one photon camera.

Example 13. Apparatus according to any of Examples 1-12, wherein the generation of the synthetic spectrum comprises utilization of a photon detection efficiency of the at least one photon camera.

Example 14. A system for radiopharmaceutical quantification of a body part, comprising:
a photon acquisition unit;
an apparatus for radiopharmaceutical quantification of a body part according to any of the preceding claims; and
an output unit;
wherein, the photon acquisition unit comprises at least one photon camera, and wherein the photon acquisition unit is configured to provide the at least one photon image; and
wherein, the output unit is configured to output an image that comprises the spatial distribution of the at least one radiopharmaceutical in the body part.

Example 15. A method for radiopharmaceutical quantification of a body part, comprising:
(a) providing a processing unit with at least one photon image of a body part; wherein, the at least one photon image was acquired by at least one photon camera configured to detect gamma rays and/or X-rays; and wherein, the at least one photon image comprises spectral energy data that comprises data that has resulted from the decay of at least one radiopharmaceutical;
(b) providing the processing unit with characteristic photon emission energies and emission probabilities associated with the decay of the at least one radiopharmaceutical;
(c) determining by the processing unit an activity of the at least one radiopharmaceutical at a plurality of spatial positions in the body part, wherein, the determination for a spatial position of the plurality of spatial positions comprises:

(c1) generating a synthetic spectrum and correlating the generated synthetic spectrum to an experimental spectrum generated from the spectral energy data for at least one position in the at least one photon image that corresponds to that spatial position, and wherein, generating the synthetic spectrum comprises utilizing the photon emission energies and emission probabilities associated with the decay of the at least one radiopharmaceutical; and (d) determining by the processing unit a spatial distribution of the at least one radiopharmaceutical in the body part.

In some exemplary embodiments, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments.

These exemplary embodiments of the invention covers both, a computer program that right from the beginning uses the invention and computer program that by means of an update turns an existing program into a program that uses invention.

Further on, the computer program element might be able to provide all necessary steps to fulfill the procedure of an exemplary embodiment of the method as described above.

According to some exemplary embodiments of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to some exemplary embodiments of the present invention, a medium for making a computer program element available for downloading is provided, which computer program element is arranged to perform a method according to previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

TABLE 1

| Decay | Mode of decay | Half-life | Comment |
| --- | --- | --- | --- |
| $^{227}$TH -> $^{223}$Ra | Alpha | 18.7 d | — |
| $^{223}$Ra -> $^{219}$Rn | Alpha | 11.4 d | — |
| $^{219}$Rn -> $^{215}$Po | Alpha | 4.0 s | — |
| $^{215}$Po -> $^{211}$Pb | Alpha | 1.8 ms | No photons emitted |
| $^{211}$Pb -> $^{211}$Bi | Beta minus | 36 min | — |
| $^{211}$Bi -> $^{207}$Tl | Alpha | 2.1 min | — |
| $^{207}$Tl -> $^{207}$Pb | Beta minus | 4.8 min | No photons emitted |
| $^{207}$Pb | NA | NA | $^{207}$Pb is stable |

The invention claimed is:

1. An apparatus for radiopharmaceutical quantification of a body part, comprising
a processor configured to:
receive from an input at least one gamma image of a body part, wherein the at least one gamma image was acquired by at least one gamma camera configured to detect gamma rays and/or X-rays and wherein the at least one gamma image comprises spectral energy data that comprises data that has resulted from decay of at least a first radiopharmaceutical and a second radiopharmaceutical;
receive from the input characteristic photon emission energies and emission probabilities associated with the decay of at least the first radiopharmaceutical and the second radiopharmaceutical;
determine an activity of at least the first radiopharmaceutical and the second radiopharmaceutical at a plurality of spatial positions in the body part,
wherein the determination for a spatial position of the plurality of spatial positions comprises a correlation of a generated synthetic spectrum to an experimental spectrum generated from the spectral energy data for at least one position in the at least one gamma image that corresponds to that spatial position, and wherein generation of the synthetic spectrum comprises utilization of the photon emission energies and emission probabilities associated with the decay of at least the first radiopharmaceutical and the second radiopharmaceutical; and
determine a spatial distribution of at least the first radiopharmaceutical and the second radiopharmaceutical in the body part.

2. The apparatus of claim 1, wherein the processor is configured to receive from the input half-lives for the decay of at least the first radiopharmaceutical and the second radiopharmaceutical, and wherein the generation of the synthetic spectrum comprises utilization of the half-lives for the decay of at least the first radiopharmaceutical and the second radiopharmaceutical.

3. The apparatus of claim 1, wherein the second radiopharmaceutical is a product of the decay of the first radiopharmaceutical.

4. The apparatus of claim 3, wherein the processor is configured to receive from the input at least one time of acquisition of the at least one gamma image relative to a start time, the start time defined as a time when the first radiopharmaceutical has not yet decayed to produce significant quantities of the second radiopharmaceutical, and wherein the generation of the synthetic spectrum comprises utilization of the at least one time of acquisition of the at least one gamma image relative to the start time.

5. The apparatus of claim 1, wherein the generation of the synthetic spectrum comprises a determination of an attenuation of photons in the body part.

6. The apparatus of claim 1, wherein the at least one gamma image comprises a first image and a second image, wherein the first image was acquired from a direction opposite a direction from which the second image was acquired.

7. The apparatus of claim 6, wherein the processor is configured to receive from the input a plurality of total thicknesses of the body part for the plurality of spatial positions; and wherein generation of the synthetic spectrum comprises utilization of a total thickness of the body part at that spatial position.

8. The apparatus of claim 6, wherein the at least one gamma camera comprises a first gamma camera and a second gamma camera.

9. The apparatus of claim 1, wherein the generation of the synthetic spectrum comprises determination of a spectral energy scatter component.

10. The apparatus of claim 1, wherein the generation of the synthetic spectrum comprises determination of a spectral energy residual component.

11. The apparatus of claim 1, wherein the generation of the synthetic spectrum comprises utilization of an energy resolution of the at least one gamma camera.

12. The apparatus of claim 1, wherein the generation of the synthetic spectrum comprises utilization of a photon detection efficiency of the at least one gamma camera.

13. A system for radiopharmaceutical quantification of a body part, comprising:
a photon acquisition unit comprising at least one gamma camera, wherein the photon acquisition unit is configured to provide the at least one gamma image;
an apparatus for radiopharmaceutical quantification of a body part comprising a processor configured to:
receive from the photon acquisition unit at least one gamma image, wherein the at least one gamma image was acquired by at least one gamma camera configured to detect gamma rays and/or X-rays, and wherein the at least one gamma image comprises spectral energy data that comprises data that has resulted from decay of at least a first radiopharmaceutical and a second radiopharmaceutical;
receive characteristic photon emission energies and emission probabilities associated with the decay of at least the first radiopharmaceutical and the second radiopharmaceutical;
determine an activity of at least the first radiopharmaceutical and the second radiopharmaceutical at a plurality of spatial positions in the body part,
wherein the determination for a spatial position of the plurality of spatial positions comprises a correlation of a generated synthetic spectrum to an experimental spectrum generated from the spectral energy data for at least one position in the at least one gamma image that corresponds to that spatial position, and wherein generation of the synthetic spectrum comprises utilization of the photon emission energies and emission probabilities associated with the decay of at least the first radiopharmaceutical and the second radiopharmaceutical;
determine a spatial distribution of at least the first radiopharmaceutical and the second radiopharmaceutical in the body part; and
an output configured to output an image that comprises the spatial distribution of at least the first radiopharmaceutical and the second radiopharmaceutical in the body part.

14. A method for radiopharmaceutical quantification of a body part, comprising:
receiving by a processor at least one gamma image of a body part wherein the at least one gamma image was acquired by at least one gamma camera configured to detect gamma rays and/or X-rays and wherein the at least one gamma image comprises spectral energy data that comprises data that has resulted from decay of at least a first radiopharmaceutical and a second radiopharmaceutical;
receiving by the processor characteristic photon emission energies and emission probabilities associated with the decay of at least the first radiopharmaceutical and the second radiopharmaceutical; and
determining by the processor an activity of at least the first radiopharmaceutical and the second radiopharmaceutical at a plurality of spatial positions in the body part, wherein the determination for a spatial position of the plurality of spatial positions comprises:
generating a synthetic spectrum and correlating the generated synthetic spectrum to an experimental spectrum generated from the spectral energy data for at least one position in the at least one gamma image that corresponds to that spatial position, and wherein generating the synthetic spectrum comprises utilization the photon emission energies and emission probabilities associated with the decay of at least the first radiopharmaceutical and the second radiopharmaceutical; and
determining by the processor a spatial distribution of at least the first radiopharmaceutical and the second radiopharmaceutical in the body part.

15. A non-transitory computer readable medium comprising instructions that, when executed by a processor, cause the processor to:
receive at least one gamma image of a body part, wherein the at least one gamma image was acquired by at least one gamma camera configured to detect gamma rays and/or X-rays, and wherein the at least one gamma image comprises spectral energy data that comprises data that has resulted from decay of at least a first radiopharmaceutical and a second radiopharmaceutical;

receive characteristic photon emission energies and emission probabilities associated with the decay of at least the first radiopharmaceutical and the second radiopharmaceutical; and determine an activity of at least the first radiopharmaceutical and the second radiopharmaceutical at a plurality of spatial positions in the body part, wherein the determination for a spatial position of the plurality of spatial positions comprises:
- generating a synthetic spectrum and correlating the generated synthetic spectrum to an experimental spectrum generated from the spectral energy data for at least one position in the at least one gamma image that corresponds to that spatial position, and wherein generating the synthetic spectrum comprises utilizing the photon emission energies and emission probabilities associated with the decay of at least the first radiopharmaceutical and the second radiopharmaceutical; and
- determining a spatial distribution of at least the first radiopharmaceutical and the second radiopharmaceutical in the body part.

* * * * *